(12) United States Patent
Xu et al.

(10) Patent No.: US 9,035,107 B2
(45) Date of Patent: May 19, 2015

(54) DEHYDROGENATION PROCESS

(75) Inventors: Teng Xu, Houston, TX (US); Stuart L. Soled, Pittstown, NJ (US); Edward A. Lemon, Easton, PA (US); Joseph E. Baumgartner, Califon, NJ (US); Sabato Miseo, Pittstown, NJ (US); George H. Gamble, Long Valley, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 117 days.

(21) Appl. No.: 13/515,057

(22) PCT Filed: Dec. 17, 2010

(86) PCT No.: PCT/US2010/061008
§ 371 (c)(1),
(2), (4) Date: Aug. 17, 2012

(87) PCT Pub. No.: WO2011/096992
PCT Pub. Date: Aug. 11, 2011

(65) Prior Publication Data
US 2012/0323046 A1   Dec. 20, 2012

Related U.S. Application Data

(60) Provisional application No. 61/301,794, filed on Feb. 5, 2010.

(30) Foreign Application Priority Data

Mar. 23, 2010  (EP) .................................... 10157370

(51) Int. Cl.
| | | |
|---|---|---|
| *C07C 37/06* | (2006.01) | |
| *B01J 23/42* | (2006.01) | |
| *B01J 21/08* | (2006.01) | |
| *B01J 37/02* | (2006.01) | |
| *C07C 5/367* | (2006.01) | |
| *C07C 37/07* | (2006.01) | |
| *C07C 37/08* | (2006.01) | |

(52) U.S. Cl.
CPC *B01J 23/42* (2013.01); *B01J 21/08* (2013.01); *B01J 37/0203* (2013.01); *C07C 5/367* (2013.01); *C07C 37/07* (2013.01); *C07C 37/08* (2013.01); *C07C 2523/58* (2013.01)

(58) Field of Classification Search
USPC .................. 568/300, 772, 799, 806
See application file for complete search history.

(56) References Cited

U.S. PATENT DOCUMENTS

| | | | |
|---|---|---|---|
| 3,534,110 A * | 10/1970 | Le Page et al. ............... | 568/799 |
| 3,856,661 A | 12/1974 | Sugier et al. | |
| 4,016,049 A | 4/1977 | Fozzard et al. | |
| 4,019,965 A | 4/1977 | Fozzard | |
| 4,021,490 A | 5/1977 | Hudson | |
| 4,115,204 A | 9/1978 | Murtha et al. | |
| 4,115,205 A | 9/1978 | Murtha | |
| 4,115,206 A | 9/1978 | Murtha | |
| 4,115,207 A | 9/1978 | Murtha | |
| 4,139,570 A * | 2/1979 | Antos .......................... | 585/434 |
| 4,167,456 A | 9/1979 | Murtha | |
| 4,201,632 A | 5/1980 | Murtha | |
| 4,230,638 A | 10/1980 | Murtha | |
| 4,933,507 A | 6/1990 | Inoki et al. | |
| 5,232,580 A * | 8/1993 | Le et al. ....................... | 208/114 |
| 7,538,066 B2 | 5/2009 | Soled et al. | |
| 7,579,511 B1 * | 8/2009 | Dakka et al. .................. | 585/316 |
| 7,605,107 B2 * | 10/2009 | Soled et al. .................... | 502/216 |
| 8,487,140 B2 * | 7/2013 | Buchanan et al. ............ | 568/799 |

FOREIGN PATENT DOCUMENTS

| | | |
|---|---|---|
| CN | 1490293 | 4/2004 |
| GB | 514 587 | 11/1939 |
| JP | 58-067636 | 4/1983 |
| WO | WO 2009/131769 | 10/2009 |
| WO | WO 2011/096993 | 8/2011 |
| WO | WO 2011/096997 | 8/2011 |
| WO | WO 2011/096999 | 8/2011 |

OTHER PUBLICATIONS

Saito et al., "*Performance of Activity Test on Supported Pd Catalysts for Dehydrogenation of Cyclohexanone to Phenol (Effect of Supports on Activity)*", Ibaraki Kogyo Koto Senmon Gakko Kenkyu Iho, 1995, vol. 30, pp. 39-46—English Abstract Only.

* cited by examiner

*Primary Examiner* — Sudhakar Katakam
*Assistant Examiner* — Pancham Bakshi
(74) *Attorney, Agent, or Firm* — Siwen Chen; Stephen Baehl

(57) ABSTRACT

In a process for the dehydrogenation of dehydrogenatable hydrocarbons, a feed comprising dehydrogenatable hydrocarbons is contacted with a catalyst comprising a support and a dehydrogenation component under dehydrogenation conditions effective to convert at least a portion of the dehydrogenatable hydrocarbons in the feed. The catalyst is produced by a method comprising treating the support with a liquid composition comprising the dehydrogenation component or a precursor thereof and at least one organic dispersant selected from an amino alcohol and an amino acid.

24 Claims, 2 Drawing Sheets

Figure 1(a)  Figure 1(b)
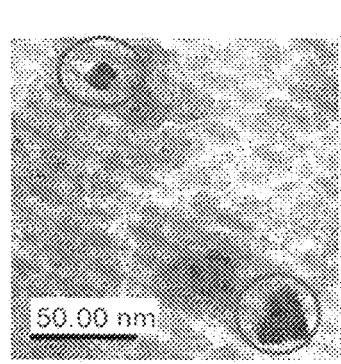
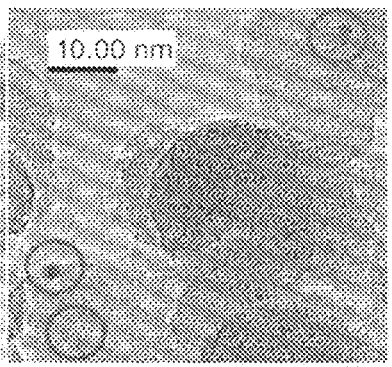
Figure 2
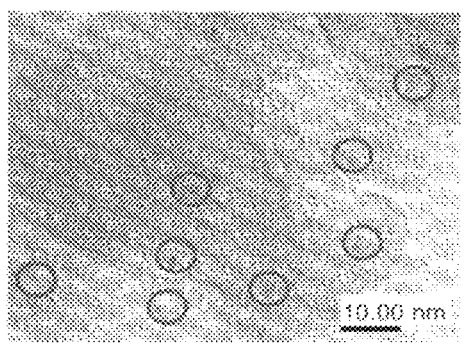

DEHYDROGENATION PROCESS

PRIORITY CLAIM

This patent application is a National Stage Application of International Application No. PCT/US2010/061008 filed Dec. 17, 2010, which claims priority to U.S. Provisional Application Ser. No. 61/301,794, filed Feb. 5, 2010, and European Application No. 10157370.7, filed Mar. 23, 2010, the disclosures of which are fully incorporated herein by their reference.

CROSS REFERENCE TO RELATED APPLICATIONS

This patent application is related to U.S. Provisional application Ser. No. 61/301,780, filed Feb. 5, 2010; U.S. Provisional Application Ser. No. 61/301,786, filed Feb. 5, 2010; and U.S. Provisional Application Ser. No. 61/301,799, filed Feb. 5, 2010, the disclosures of which are fully incorporated herein by their reference.

FIELD

The present invention relates to a process for dehydrogenating a dehydrogenatable hydrocarbon.

BACKGROUND

Various dehydrogenation processes have been proposed to dehydrogenate dehydrogenatable hydrocarbons such as cyclohexanone and cyclohexane. For example, these dehydrogenation processes have been used to convert at least a portion of cyclohexanone into phenol.

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone.

Other known routes for the production of phenol involve the direct oxidation of benzene, the oxidation of toluene, and the oxidation of s-butylbenzene wherein methyl ethyl ketone is co-produced with phenol in lieu of acetone produced in the Hock process.

Additionally, phenol can be produced by the oxidation of cyclohexylbenzene to cyclohexylbenzene hydroperoxide wherein cyclohexanone is co-produced with phenol in lieu of acetone produced in the Hock process. A producer using this process may desire to dehydrogenate at least a portion of the cyclohexanone produced into the additional phenol depending on market conditions.

There are many methods for dehydrogenating various compounds into phenol. For example, U.S. Pat. No. 4,933,507 discloses that phenol can be produced by dehydrogenating cyclohexenone through a vapor-phase reaction in the presence hydrogen using a solid-phase catalyst having platinum and an alkali metal carried on a support such as silica, silica-alumina or alumina. In addition, Saito et al. discloses the use of palladium supported on various metal oxides ($Al_2O_3$, $TiO_2$, $ZrO_2$, MgO) as a catalyst in the dehydrogenation of cyclohexanone to phenol. See "Performance of Activity Test on Supported Pd Catalysts for Dehydrogenation of Cyclohexanone to Phenol (effect of supports on activity)", *Ibaraki Kogyo Koto Senmon Gakko Kenkyu Iho* (1995), 30, pp. 39-46.

One problem that has been encountered in the use of supported noble metal catalysts in the dehydrogenation of compounds such as cyclohexanone is that the activity of the noble metal decreases fairly rapidly unless the metal is well dispersed on the support. However, a typical catalyst produced by directly impregnating a noble metal onto a support tends to result in poor metal dispersion because of non-uniform metal particle sizes. Thus, the resultant catalyst generally deactivates rapidly and so requires frequent reactivation or replacement. Given the high cost of noble metals and the loss in production time involved with frequent reactivation, there is therefore a need for a cyclohexanone dehydrogenation catalyst having improved resistance to deactivation.

According to the present invention, it has now been found that, by adding an amino acid or amino alcohol to the liquid vehicle used to deposit the noble metal onto the support, the dispersion of the noble metal on the support can be improved resulting in a more deactivation-resistant catalyst.

U.S. Pat. No. 7,538,066 discloses a supported multi-metallic catalyst for use in the hydroprocessing of hydrocarbon feeds, wherein the catalyst is prepared from a catalyst precursor comprising at least one Group VIII metal, a Group VI metal and an organic agent selected from the group consisting of amino alcohols and amino acids. The catalyst precursor is thermally treated to partially decompose the organic agent, then sulfided. The addition and subsequent partial decomposition of the organic agent is said to decrease the average height of the platelet stacks of the final sulfide catalyst.

SUMMARY

In one aspect, the invention resides in a process for the dehydrogenation of at least one dehydrogenatable hydrocarbon, the process comprising contacting a feed comprising the dehydrogenatable hydrocarbon with a catalyst comprising a support and a dehydrogenation component under dehydrogenation conditions effective to convert at least a portion of the dehydrogenatable hydrocarbon in said feed, wherein the catalyst is produced by a method comprising treating the support with a liquid composition comprising said dehydrogenation component or a precursor thereof and at least one organic dispersant selected from an amino alcohol and an amino acid.

Conveniently, the dehydrogenatable hydrocarbon is an alicyclic compound such as cyclohexane and cyclohexanone which is converted into an aromatic compound such as benzene and phenol.

Conveniently, the dehydrogenatable hydrocarbon is cyclohexanone wherein at least a portion of the cyclohexanone is converted into phenol.

Conveniently, the dehydrogenatable hydrocarbon is cyclohexane wherein at least a portion of cyclohexane is converted into benzene.

Conveniently, the support is selected from the group consisting of silica, a silicate, an aluminosilicate, carbon, and carbon nanotubes.

Conveniently, the dehydrogenation component comprises at least one metal component selected from Groups 6 to 10 of the Periodic Table of Elements, such as platinum and palladium.

In one embodiment, said at least one organic dispersant comprises an amino acid, especially arginine.

Conveniently, the catalyst further contains an inorganic base component comprising a metal component selected from an alkali metal, an alkaline earth metal, an alkali metal compound, and an alkaline earth metal compound, especially potassium or a potassium compound. The catalyst may be treated with the dehydrogenation component and the inorganic base component in any sequence or simultaneously wherein the organic dispersant may be used when treating with the dehydrogenation component or the inorganic component, or both.

Conveniently, wherein the method of producing the catalyst further comprises heating the treated support in an oxidizing atmosphere under conditions to decompose substantially all of said organic dispersant.

Conveniently, the dehydrogenation conditions include a temperature of about 250° C. to about 750° C., a pressure of about atmospheric to about 500 psig (100 to 3550 kPa), a weight hourly space velocity of about 0.2 to about 50 $hr^{-1}$, and a hydrogen to cyclohexanone-containing feed molar ratio of about 2 to about 20.

In a further aspect, the invention resides in a process for producing phenol from benzene, the process comprising:

(a) contacting benzene and hydrogen with a catalyst under hydroalkylation conditions to produce cyclohexylbenzene;

(b) oxidizing at least a portion of cyclohexylbenzene from (a) to produce cyclohexylbenzene hydroperoxide;

(c) converting at least a portion of cyclohexylbenzene hydroperoxide from (b) to produce an effluent steam comprising phenol and cyclohexanone; and (d) contacting at least a portion of said effluent stream with a catalyst comprising a support and a dehydrogenation component under dehydrogenation conditions effective to convert at least a portion of the cyclohexanone in said feed into phenol and hydrogen, wherein the catalyst is produced by a method comprising treating the support with a liquid composition comprising said dehydrogenation component or a precursor thereof and at least one organic dispersant selected from an amino alcohol and an amino acid.

BRIEF DESCRIPTION OF THE DRAWINGS

FIGS. 1(a) and (b) are transmission electron micrographs (TEM) of the 1% Pt/$SiO_2$ catalyst of Example 5 at on-screen magnifications of 57,000 times and 110,000 times respectively.

FIG. 2 is a transmission electron micrograph of the 1% Pt/$SiO_2$ catalyst (with arginine dispersion) of Example 6 at an on-screen magnification of 110,000 times.

DETAILED DESCRIPTION OF THE EMBODIMENTS

Figure 3:
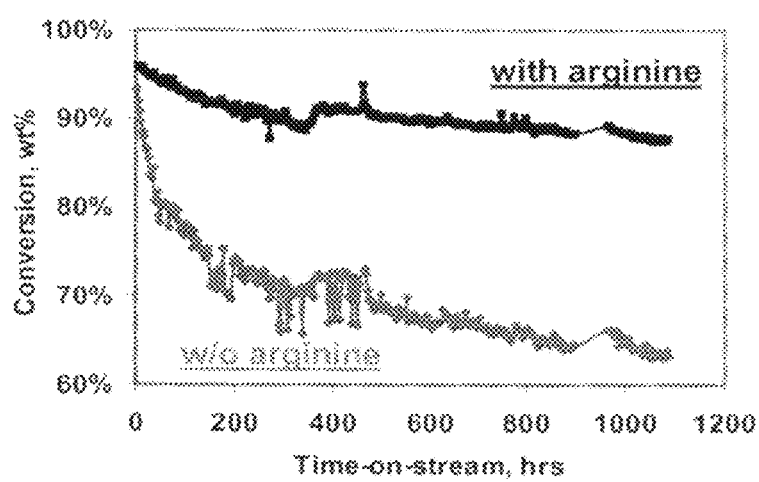
FIG. 3 compares the cyclohexanone conversion against time on stream for the catalysts of Examples 5 and 6.

Described herein is a process for dehydrogenating at least one dehydrogenatable hydrocarbon such as cyclohexanone. Specifically, this dehydrogenation process can be utilized in a phenol process wherein cyclohexanone is co-produced by allowing the at least a portion of the co-produced cyclohexanone to be converted to additional phenol. In the phenol process wherein cyclohexanone is co-produced, cyclohexylbenzene, generally produced by the catalytic hydroalkylation of benzene, is oxidized to produce cyclohexylbenzene hydroperoxide and then the cyclohexylbenzene hydroperoxide is cleaved to produce an effluent stream comprising phenol and cyclohexanone in substantially equimolar amounts. At least a portion of the effluent is then fed to a dehydrogenation reaction zone, where the effluent stream portion is contacted with a dehydrogenation catalyst so as to convert the cyclohexanone in said effluent portion into additional phenol and into hydrogen, which can be recycled to the benzene hydroalkylation step.

Dehydrogenation Catalyst and Process

The dehydrogenation catalyst comprises a support, typically formed of silica, a silicate, an aluminosilicate, carbon, or carbon nanotubes, on which is deposited a dehydrogenation component, typically comprising at least one metal component selected from Groups 6 to 10 of the Periodic Table of Elements.

As used herein, the numbering scheme for the Periodic Table Groups is as disclosed in Chemical and Engineering News, Vol. 63(5), p. 27 (1985).

In one embodiment, dehydrogenation component comprises at least one metal component selected from Groups 6 to 10 of the Periodic Table of Elements, such as platinum and palladium such that the dehydrogenation component may comprise any combination or mixture of metal components selected from Groups 6 to 10 of the Periodic Table of Elements. In another embodiment, the dehydrogenation component comprises at least one metal component selected from Group 10 of the Periodic Table of Elements. In other embodiments, the dehydrogenation component consists of one metal component selected from Group 6 to Group 10 of the Periodic Table of Elements; one metal component selected from Group 10 of the Periodic Table of Elements; or one metal component selected from palladium and platinum. In still another embodiment, the catalyst consists of a support and a dehydrogenation component selected from Group 10 of the Periodic Table of Elements. Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

In one embodiment, the dehydrogenation catalyst comprises a silica support having pore volumes and median pore diameters determined by the method of mercury intrusion porosimetry described by ASTM Standard Test D4284. The silica support may have surface areas as measured by ASTM D3663. In one embodiment, the pore volumes are in the range of from about 0.2 cc/gram to about 3.0 cc/gram. The median pore diameters are in the range from about 10 angstroms to about 2000 angstroms or from about 20 angstroms to about 500 angstroms; and the surface areas (m2/gram) are in the range from about 10 m2/gram to about 1000 m2/gram or from about 20 m2/gram to about 500 m2/gram. The support may or may not comprise a binder.

In one embodiment, the catalyst further contains an inorganic base component comprising a metal component selected from an alkali metal, an alkaline earth metal, an alkali metal compound, and an alkaline earth metal compound, especially potassium or a potassium compound. In another embodiment, the catalyst further contains an inorganic base component comprising a metal component selected from Group 1 and Group 2 of the Periodic Table of Elements. Typically, the inorganic base component is present in an amount between about 0.1 wt % and about 5 wt % of the catalyst.

The term "metal component" is used herein to include a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

The dehydrogenation catalyst may be used to dehydrogenate any dehydrogenatable hydrocarbon such as an alicyclic compound. "Dehydrogenatable hydrocarbon" refers to all classes of hydrocarbons containing saturated carbon bonds which have the potential for forming one or more unsaturated bonds through the process of dehydrogenation. "Alicyclic compounds" refers to saturated or unsaturated non-aromatic hydrocarbon ring systems containing from three to twenty ring carbon atoms wherein the hydrocarbon ring system may also have a side-chain or a functional group attached directly to or bound within the ring. Examples of alicyclic compounds include, without limitation, cyclopropane, cyclopentane, methyl cyclopentane, cyclobutane, cyclopentene, cyclodecane, cyclohexane, methylcyclohexane, cyclododecane, and six carbon ring alicyclic compounds such as cyclohexane. Other examples of alicyclic compounds include without limitation alicyclic ketones such as cyclohexanone and alicyclic alcohols such as cyclohexanol.

In one embodiment, at least a portion of the six carbon ring alicyclic compounds are dehydrogenated (or converted) to aromatic compounds such as benzene and phenol. For example, at least a portion of cyclohexanone may be dehydrogenated to phenol and at least a portion of cyclohexane may be dehydrogenated to benzene.

In another embodiment, at least a portion of the alicyclic compounds are (i) dehydrogenated to unsaturated compounds; (ii) rearranged to form other alicyclic compounds; or (iii) fragment to lighter hydrocarbons.

The present dehydrogenation catalyst is prepared by initially treating the support, normally by impregnation, with a liquid composition comprising the dehydrogenation component or a precursor thereof, the optional inorganic base component and at least one organic dispersant selected from an amino alcohol and an amino acid. The organic dispersant may be dispersed in a liquid carrier. The liquid carrier is generally water. Examples of amino alcohols include wherein the amino alcohol is selected from the group consisting of methanolamine, dimethanolamine, tri-methanolamine, ethanolamine, di-ethanolamine, triethanolamine, butanolamine, dibutanolamine, tributanolamine, propanolamine, dipropanaolamine, tripropanolamine, N,N,-dialkyl-ethanolamines, N-alkyl-diethanolamines, N-alkyl-ethanolamines, N,N,-dialkyl-propanolamines, N-alkyl-dipropanolamines, N-alkyl-propanolamines, N,N,-dialkyl-propanolamines, N-alkyl-dipropanolamines, N-alkyl-propanolamines, N,N,-dialkyl-propanolamines, N-alkyl-dipropanolamines, N-alkyl-propanolamines, N,N,-dialkyl-butonolamines, N-alkyl-dibutanolamines, N-alkyl-butanolamines, N,N,-dialkyl-butanolamines, N-alkyl-dibutanolamines, N-alkyl-butanolamines, N,N,-dialkyl-hexanolamines, N-alkyl-dihexanolamines, N-alkyl-hexanolamines, N,N,-dialkyl-hexanolamines, N-alkyl-dihexanolamines, N-alkyl-hexanolamines, N,N,-dialkyl-heptanolamines, N-alkyl-diheptanolamines, N-alkyl-heptanolamines, N,N,-dialkyl-heptanolamines, N-alkyl-diheptanolamines, N-alkyl-heptanolamines Examples of amino acids include alanine, arginine, asparagines, aspartic acid, cysteine, cystine, 3,5-dibromotyrosine, 3,5, diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, with arginine being preferred.

Generally, the organic dispersant is present in the liquid composition in an amount between about 1 wt % and about 20 wt % of the composition, preferably in an amount between about 2 wt % and about 10 wt %, more preferably in an amount between about 5 wt % to about 10 wt %. In one embodiment, after treatment with the liquid composition, the support is dried to remove the liquid carrier and is then heated in an oxidizing atmosphere, generally in air, under conditions to decompose substantially all of said organic dispersant. "Decompose substantially all of said organic dispersant" generally means that any remaining organic dispersant left on the support will not materially affect the catalyst dehydrogenation activity. In another embodiment, after treatment with the liquid composition, the support is dried to remove the liquid carrier and is then heated in an oxidizing atmosphere, generally in air, under conditions to decompose essentially all of said organic dispersant. "Decompose essentially all of said organic dispersant" generally means that the organic dispersant cannot be detected on the support by infrared spectroscopy. Suitable conditions for removing the dispersant include a temperature of about 100° C. to about 600° C. for a time of about 0.5 to about 50 hours. The catalyst may then be heated in a reducing atmosphere, such as hydrogen, at a temperature of about 50° C. to about 500° C. for a time of about 0.5 to about 10 hours to reduce the dehydrogenation component.

It is found that adding the organic dispersant to the liquid composition used to deposit the dehydrogenation metal on the support results in a catalyst with improved metal dispersion measured by oxygen chemisorption, with the catalyst produced by the present method typically exhibiting oxygen chemisorption values greater than about 30% and less than about 90%.

In other embodiments, the catalyst has an oxygen chemisorption of greater than about 30%, greater than about 40%, greater than about 50%, greater than about 60%, greater than about 70%, and greater than about 80%.

In one embodiment, the Dsv (surface-volume-averaged diameter) of the dehydrogenation component is less than 5 nm as measured by transmission electron micrograph (TEM). Preferably, the Dsv of the dehydrogenation component is from 0.1 nm to 5 nm. In other embodiments, the Dsv lower limit may be 0.1 nm, 0.2 nm, 0.3 nm, 0.4 nm, 0.5 nm, 1 nm, 1.2 nm. 1.5 nm, 1.7 nm, and 2.0 nm; and the upper limit Dsv may be 3 nm, 3.2 nm, 3.5 nm, 3.7 nm, 4.0 nm, 4.5 nm, and 5 nm with ranges from any lower limit to any upper limit being contemplated.

As used herein, the Dsv (surface-volume-averaged diameter) for the catalysts is measured by collecting about 20 to about 80 random images of a given catalyst with a Philips CM 12 or Philips CM 200 transmission electron microscope operated at 120 kV and 200 kV (or equivalent) at screen magnifications of 57,000 to 110,000. For purposes of the experiments, the data were collected as digital images with a Gatan CCD camera system using Gatan's Digital Micrograph program, v. 2.5. The line drawing tool in the Digital Micrograph program was used to mark the diameter of each imaged metal particle from which a statistically determined Dsv is obtained. To calculate the Dsv, a histogram of the distribution of particle sizes is obtained from the TEM (transmission electron microscope) measurements, and from the histogram the Dsv is obtained by the following equation:

$$Dsv = \{\mathrm{sum}(N_i D_i^3)\}/\{\mathrm{sum}(N_i D_i^2)\}$$

where $N_i$ is the number of particles with a diameter $D_i$.

As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique.

Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [11 kPa to 53 kPa]) is measured at 40° C. with $O_2$ as the adsorbent molecule. Extrapolation of the linear portion of this curve to zero pressure gives the total or combined adsorption uptake.

Suitable conditions for the dehydrogenation comprise a temperature of about 250° C. to about 750° C. and a pressure of about 0.01 atm to about 20 atm (1 kPa to 2000 kPa), such as a temperature of about 300° C. to about 500° C. and a pressure of about 1 atm to about 3 atm (100 kPa to 300 kPa).

The reactor configuration used for the dehydrogenation process generally comprises one or more fixed bed reactors containing a solid catalyst with a dehydrogenation function. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

Production of Cyclohexylbenzene

The cyclohexylbenzene employed in the present process can be produced by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting benzene with hydrogen under hydroalkylation conditions in the presence of a hydroalkylation catalyst whereby the benzene undergoes the following reaction (1) to produce cyclohexylbenzene (CHB):

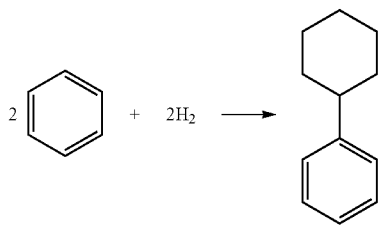
(1)

Details of such a process for producing cyclohexylbenzene can be found in paragraphs [0027] through [0038] of WO 2009/131769, the disclosure of which is hereby incorporated by reference.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Details of such a process for producing cyclohexylbenzene can be found in paragraphs [0048] through [0055] of WO 2009/131769, the disclosure of which is hereby incorporated by reference.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 kPa to about 2,500 kPa, such as about 100 kPa to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

Details of such a process for hydroperoxide cleavage can be found in paragraphs [0056] through [0075] of WO 2009/131769, the disclosure of which is hereby incorporated by reference.

Treatment of Cleavage Effluent

The effluent from the cleavage reaction comprises phenol and cyclohexanone in substantially equimolar amounts. The present process provides an advantageous route to increasing the amount of phenol produced from the original benzene feed by contacting at least a portion of the cleavage effluent with a dehydrogenation catalyst so as to convert some or all of the cyclohexanone in the effluent into additional phenol according to the reaction (2):

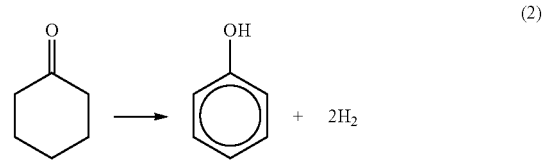
(2)

In one embodiment, the dehydrogenation catalyst and process described herein may be used in reaction (2).

Cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. However, the efficiency of the separation can be enhanced by conducting the distillation under at least partial vacuum, typically at below 101 kPa. Moreover, extractive distillation processes are known for separating cyclohexanone and phenol, see for example, U.S. Pat. Nos. 4,021,490; 4,019,965; 4,115,207; 4,115,204; 4,115,206; 4,201,632; 4,230,638; 4,167,456; 4,115,205; and 4,016,049. Nevertheless, phenol/cyclohexanone separation remains a costly process, so that in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The first separation step is conveniently effected by vacuum distillation and the same, or additional vacuum distillation steps, can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

By employing the present dehydrogenation process, substantially all the cyclohexanone in the cyclohexylbenzene hydroperoxide cleavage effluent can be converted to phenol. In practice; however, depending on market conditions, there is likely to be a significant demand for cyclohexanone product. This can readily be met by using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

The invention will now be more particularly described with reference to the following non-limiting Examples and the accompanying drawing.

The silica used in the following examples was Sigma-Aldrich Davison grade 62, 60-200 mesh, 150 angstrom.

EXAMPLE 1

Synthesis of 1% Pt/SiO$_2$ Catalyst 11.2 g of tetraamine platinum (II) hydroxide solution containing 4.49 wt % of Pt was mixed with 61.1 g of deionized water. The mixture was added dropwise to 50.0 g of silica, and the resulting mixture was mixed well. The sample was dried at 120° C. for 2 hours. 10 g of the dried sample was then calcined in an oven by ramping the temperature at a rate of 3° C./minute to 350° C. and maintaining the oven temperature at 350° C. for 16 hrs in 300 standard cubic centimeter per minute (sccm) of air. The calcined sample was denoted as 1% Pt/SiO$_2$.

EXAMPLE 2

Synthesis of 1% Pt/SiO2 Catalyst with Arginine 2.23 g of tetraamine platinum (II) hydroxide solution containing 4.49 wt % of Pt was mixed with 12.2 g of deionized water. 0.75 g of arginine was added to the mixture. The mixture was then added dropwise to 10.0 g of silica, and the resulting mixture was mixed well. The sample was dried at 120° C. for 2 hrs. The dried sample was then calcined in an oven by ramping the temperature at a rate of 3° C./minute to 400° C. and maintaining the oven temperature at 400° C. for 16 hrs in 300 sccm of air. The calcined sample was denoted as 1% Pt/SiO2 with arginine.

EXAMPLE 3

Oxygen Chemisorption of 1% Pt/SiO of Example 1

The product of Example 1 was prepared for oxygen chemisorption measurement by heating the sample to 130° C. at 4° C./minute and holding for 60 minutes in helium. The helium supply was then turned off, and H$_2$ was switched on. The sample was heated to 425° C. at 2° C./min in H$_2$ and held for 120 minutes at 425° C. The sample was cooled to 400° C. and was evacuated for 30 minutes. The sample was then cooled to 40° C. in vacuum. The measured oxygen chemisorption value for the sample is 27%.

EXAMPLE 4

Oxygen Chemisorption of 1% Pt/SiO$_2$ with Argnine of Example 2

The oxygen chemisorption test of Example 3 was repeated on the catalyst of Example 2. The measured value for the sample is 54%. The chemisorption values strongly suggest that the sample prepared with arginine has much higher Pt dispersion than the sample prepared without arginine.

EXAMPLE 5

TEM of 1% Pt/SiO$_2$ of Example 1

FIG. 1 shows two TEM images for the 1% Pt/SiO$_2$ of Example 1. Prior to the TEM studies, the sample was reduced following a similar procedure used for oxygen chemisorption to ensure that Pt particles were properly reduced to metal form. Note the sample has non-uniform Pt particles. Particles as large as about 20 nm and as small as around 2 nm were observed in the sample. The particle Dsv observed was greater than 5 nm.

EXAMPLE 6

TEM of 1% Pt/SiO2 with Arginine of Example 2

The same reduction procedure was followed as that used for TEM study of Pt/SiO2 sample. The TEM image is shown in FIG. 2. Note that the Pt particles are relatively uniform, and are much smaller than those shown in FIG. 1. The particle Dsv observed was approximately 2 to 3 nm in the sample.

EXAMPLE 7

Performance comparison of 1% Pt/SiO2 with and without Arginine

Samples of the products of examples 1 and 2 were pressed into thin catalyst disks using a hydraulic press. The thin catalyst disks were crushed and sieved. Catalyst particles between 400 to 600 microns were collected for catalyst testing.

600 mg of each pelletized catalyst was mixed with 3.5 g of about 400 micron quartz chips, and the mixture was packed into a 3/8" (0.95 cm) stainless steel reactor. A thermocouple was inserted from the bottom of the reactor into the center of the roughly 5" (12.7 cm) catalyst bed for measuring catalyst bed temperature. Cyclohexanone feed was delivered at 9.5 ml/hr using an ISCO pump. Cyclohexanone feed was vaporized prior to mixing with 72 sccm of H$_2$. The mixture was fed into a downflow reactor. The reaction was run at 425° C. and 100 psi, gauge (psig) (791 kPa) total reactor pressure, so the cyclohexanone partial pressure was 37 psi-absolute (psia) (255 kPa). The weight hourly space velocity (WHSV) worked out to be approximately 15 hr$^{-1}$. The H2/cyclohexanone molar ratio of the feed was 2 to 1.

Prior to the introduction of cyclohexanone feed, each catalyst was pretreated in 72 sccm H$_2$ at 100 psig (791 kPa) by ramping the reactor temperature from room temperature to 425° C. at 2° C./min; whereafter the reactor temperature was held at 425° C. for 3 hours under the same H$_2$ flow and pressure to allow for reduction of supported catalysts prior to testing.

The effluent from the reactor was sampled using a Valco sampling valve, and the sample was sent to an on-line GC equipped with a FID for analysis. All the hydrocarbons were analyzed and the results were normalized. H$_2$ was not included in the analysis. Conversion was calculated based on the concentration of cyclohexanone in the effluent. Cyclohexanol, which was typically present in the effluent, was counted as unreacted feed. The results are shown in FIG. 3, from which it will be seen that the sample prepared with arginine showed much higher conversion throughout the run than the sample prepared without arginine.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

In another embodiment, this disclosure relates to:

1. A process for the dehydrogenation of at least one dehydrogenatable hydrocarbon, the process comprising contacting a feed comprising the at least one dehydrogenatable hydrocarbon with a catalyst comprising a support and a dehydrogenation component under dehydrogenation conditions effective to convert at least a portion of the at least one dehydrogenatable hydrocarbon in the feed, wherein the catalyst is produced by a method comprising treating the support with a liquid composition comprising the dehydrogenation component or a precursor thereof and at least one organic dispersant selected from an amino alcohol and an amino acid.
2. The process of embodiment 1, wherein the dispersant is present in the liquid composition in an amount between about 1 wt % and about 20 wt % of the composition.
3. The process of embodiment 1, wherein the support is at least one material selected from silica, a silicate, an aluminosilicate, carbon, and carbon nanotubes.
4. The process of embodiment 1, wherein the dehydrogenation component comprises at least one metal component selected from Groups 6 to 10 of the Periodic Table of Elements.
5. The process of embodiment 1, wherein the dehydrogenation component comprises at least one metal component selected from platinum and palladium.
6. The process of embodiment 1, wherein the dehydrogenation component consists of one metal component selected from Group 10 of the Periodic Table of Elements.
7. The process of embodiment 1, wherein the dehydrogenation component consists of one metal component selected from platinum and palladium.
8. The process of embodiment 1, wherein the catalyst consists of a support and a dehydrogenation component selected from platinum and palladium.
9. The process of embodiment 1, wherein the at least one organic dispersant comprises an amino acid.
10. The process of embodiment 1, wherein the catalyst has an oxygen chemisorption of at least 30%.
11. The process of embodiment 1, wherein the catalyst has an oxygen chemisorption of at least 40%.
12. The process of embodiment 1, wherein the catalyst has an oxygen chemisorption of at least 50%.
13. The process of embodiment 1, wherein the dehydrogenation component has a Dsv of less than 5 nm as measured by TEM.
14. The process of embodiment 1, wherein the at least one organic dispersant comprises arginine.
15. The process of embodiment 1, wherein the liquid composition comprises an aqueous solution of the dehydrogenation component or precursor thereof and the at least one organic dispersant.
16. The process of embodiment 1, wherein the catalyst further contains an inorganic base component.
17. The process of embodiment 16, wherein the inorganic base component comprises at least one metal component selected from an alkali metal and an alkaline earth metal.
18. The process of embodiment 1, wherein the method of producing the catalyst further comprises heating the treated support in an oxidizing atmosphere under conditions to decompose substantially all of the organic dispersant.
19. The process of embodiment 1, wherein the method of producing the catalyst further comprises heating the treated support in an oxidizing atmosphere under conditions to decompose essentially all of the organic dispersant.
20. The process of embodiment 1, wherein the at least one dehydrogenatable hydrocarbon is an alicyclic compound.
21. The process of embodiment 1, wherein the at least one dehydrogenatable hydrocarbon is cyclohexanone.
22. The process of embodiment 1, wherein the at least one dehydrogenatable hydrocarbon is cyclohexanone and wherein at least a portion of the cyclohexanone is converted into phenol.
23. The process of embodiment 1, wherein the at least one dehydrogenatable hydrocarbon is cyclohexane.
24. The process of embodiment 1, wherein the at least one dehydrogenatable hydrocarbon is cyclohexanol.
25. The process of embodiment 1, wherein at least a portion of the at least one dehydrogenatable hydrocarbon is converted into an aromatic compound.
26. The process of embodiment 1, wherein the dehydrogenation conditions include a temperature of about 250° C. to about 500° C., a pressure of about atmospheric to about 500 psig (100 to 3550 kPa), a weight hourly space velocity of about 0.2 to about 50 hr$^{-1}$, and a hydrogen to cyclohexanone-containing feed molar ratio of about 2 to about 20.
27. A process for producing phenol from benzene, the process comprising:
    (a) contacting benzene and hydrogen with a catalyst under hydroalkylation conditions to produce cyclohexylbenzene;
    (b) oxidizing at least a portion of cyclohexylbenzene from (a) to produce cyclohexylbenzene hydroperoxide;
    (c) converting at least a portion of cyclohexylbenzene hydroperoxide from (b) to produce an effluent stream comprising phenol and cyclohexanone; and
    (d) contacting at least a portion of the effluent stream with a catalyst comprising a support and a dehydrogenation component under dehydrogenation conditions effective to convert at least a portion of the cyclohexanone in the feed into phenol and hydrogen, wherein the catalyst is produced by a method comprising treating the support with a liquid composition comprising the dehydrogenation component or a precursor thereof and at least one organic dispersant selected from an amino alcohol and an amino acid.

28. The process of embodiment 27, wherein the dehydrogenation component comprises at least one metal component selected from Groups 6 to 10 of the Periodic Table of Elements.

29. The process of embodiment 27, wherein the dehydrogenation component consists of one metal component selected from Groups 6 to 10 of the Periodic Table of Elements.

30. The process of embodiment 27, and further comprising:
(e) recycling at least a portion of the hydrogen produced in contacting (d) to the contacting (a).

The invention claimed is:

1. A process for the dehydrogenation of at least one dehydrogenatable hydrocarbon, the process comprising:
(i) producing a catalyst by treating a support with a liquid composition comprising a dehydrogenation component or a precursor thereof and at least one organic dispersant selected from an amino alcohol and an amino acid; and
(ii) contacting a feed comprising the at least one dehydrogenatable hydrocarbon with the catalyst comprising the support and the dehydrogenation component under dehydrogenation conditions effective to convert at least a portion of the dehydrogenatable hydrocarbon in the feed.

2. The process of claim 1, wherein the organic dispersant is present in the liquid composition in an amount between about 1 wt% and about 20 wt% of the composition.

3. The process of claim 1, wherein the support is at least one material selected from silica, a silicate, an aluminosilicate, carbon, and carbon nanotubes and preferably comprises silica.

4. The process of claim 1, wherein the dehydrogenation component comprises at least one metal component selected from Groups 6 to 10 of the Periodic Table of Elements.

5. The process of claim 1, wherein the dehydrogenation component consists of one metal component selected from Group 10 of the Periodic Table of Elements.

6. The process of claim 1, wherein the dehydrogenation component consists of one metal component selected from platinum and palladium.

7. The process of claim 1, wherein the catalyst consists of a support and a dehydrogenation component selected from platinum and palladium.

8. The process of claim 1, wherein the at least one organic dispersant comprises an amino acid.

9. The process claim 1, wherein the catalyst has an oxygen chemisorption of at least 30%.

10. The process of claim 1, wherein the catalyst has an oxygen chemisorption of at least 40%.

11. The process of claim 1, wherein the catalyst has an oxygen chemisorption of at least 50%, 12. The process of claim 1, wherein the dehydrogenation component has a Dsv of less than 5 nm as measured by TEM.

13. The process of claim II, wherein the liquid composition comprises an aqueous solution of the dehydrogenation component or precursor thereof and the at least one organic dispersant.

14. The process of claim 1, wherein the catalyst further comprises an inorganic base component, preferably an alkali or alkaline earth metal compound, and more preferably a potassium compound.

15. The process of claim 14, wherein the liquid composition also comprises the inorganic base component or a precursor thereof.

16. The process of claim I. wherein the method of producing the catalyst father comprises heating the treated support in an oxidizing atmosphere under oxidation. conditions to decompose substantially all of the organic dispersant.

17. The process of claim 16, wherein the oxidation conditions include a temperature of from about 250° C. to about 450° C. for a time of about 0.5 to about 50 hours.

18. The process of claim 16, wherein the method of producing the catalyst further comprises heating the treated support in a reducing atmosphere under reducing conditions.

19. The process of claim 1, wherein the at least one dehydrogenatable hydrocarbon is an alicyclic compound.

20. The process of claim 1, wherein the at least one dehydrogenate dehydrogenatabie hydrocarbon is cyclohexanone.

21. The process of claim 20, wherein at least a portion of the cyclochexanone is converted into phenol.

22. The process of claim 1, wherein the at least one dehydrogenatable hydrocarbon is cyclohexane or cyclohexanol.

23. The process of claim I, wherein at least a portion of the at least one dehydrogenatable hydrocarbon is converted into an aromatic compound.

24. A process of claim 1, the process further comprising:
(a) reacting benzene and hydrogen in the presence of a catalyst under hydroalkylation conditions to produce cyclohexylbenzene;
(b) oxidizing at least a portion of cyclohexylbenzene from (a) to produce cyclohexylbenzene hydroperoxide;
(c) converting at least a portion of cyclohexylbenzene hydroperoxide from (b) to produce an effluent stream comprising phenol and cyclohexanone; and
(d) feeding at least portion of the effluent stream to the contacting (ii).

* * * * *

UNITED STATES PATENT AND TRADEMARK OFFICE
CERTIFICATE OF CORRECTION

PATENT NO. : 9,035,107 B2  
APPLICATION NO. : 13/515057  
DATED : May 19, 2015  
INVENTOR(S) : Teng Xu et al.

Page 1 of 1

It is certified that error appears in the above-identified patent and that said Letters Patent is hereby corrected as shown below:

In the claims

At col. 14, line 7, claim 13 is amended to read:

13. The process of claim [[II]] 1, wherein the liquid composition comprises an aqueous solution of the dehydrogenation component or precursor thereof and the at least one organic dispersant.

At col. 14, lines 17-18, claim 16 is amended to read:

16. The process of claim [[I.]] 1, wherein the method of producing the catalyst further comprises heating the treated support in an oxidizing atmosphere under oxidation [[.]] conditions to decompose substantially all of the organic dispersant.

At col. 14, lines 30-31, claim 20 is amended to read:

20. The process of claim 1, wherein the at least one dehydrogenatable hydrocarbon is cyclohexanone.

At col. 14, line 36, claim 23 is amended to read:

23. The process of claim [[I]] 1, wherein at least a portion of the at least one dehydrogenatable hydrocarbon is converted into an aromatic compound.

Signed and Sealed this  
Fifteenth Day of March, 2016

Michelle K. Lee  
*Director of the United States Patent and Trademark Office*